United States Patent [19]
Funakoshi et al.

[11] 4,034,126
[45] July 5, 1977

[54] PROCESS FOR COATING GRANULAR MATERIALS

[75] Inventors: Yoshiro Funakoshi, Kyoto; Yoshihiko Matsumura, Kawanishi; Masaki Yamamoto, Suita; Hiromu Komeda, Nara, all of Japan

[73] Assignee: Takeda Chemical Industries, Ltd., Osaka, Japan

[22] Filed: Oct. 10, 1975

[21] Appl. No.: 621,621

Related U.S. Application Data

[63] Continuation-in-part of Ser. No. 419,964, Nov. 29, 1973, abandoned, which is a continuation-in-part of Ser. No. 213,608, Dec. 29, 1971, abandoned.

[30] Foreign Application Priority Data

Dec. 29, 1970 Japan .......................... 45-128947

[52] U.S. Cl. .................. 427/8; 427/213; 427/212; 118/7
[51] Int. Cl.² .......................... B05D 1/00
[58] Field of Search ............ 118/5, 7, 8, 11, 6; 427/8, 10, 212-222

[56] References Cited
UNITED STATES PATENTS

| | | | |
|---|---|---|---|
| 2,016,920 | 10/1935 | Fisher et al. | 118/8 |
| 3,141,792 | 7/1964 | Lachman et al. | 427/3 |
| 3,347,701 | 10/1967 | Yamagishi et al. | 427/8 |
| 3,671,296 | 6/1972 | Funakoshi et al. | 427/213 |
| 3,711,319 | 1/1973 | Irikura et al. | 427/213 |

*Primary Examiner*—Ronald H. Smith
*Assistant Examiner*—S. Silverberg

[57] ABSTRACT

A process for coating granular materials particularly applicable in coating granular materials each having a particle size within the range of 100 to 1,000 microns, wherein supply of a coating or binding liquid is effected in response to a specific measured electro-resistance of a fluidized means of the granular materials while supply of a coating powder is continuously effected in a predetermined variable rate. To this end, at least one electrode cooperates with a portion of the wall forming a coating apparatus to detect the specific electro-resistance which is in turn compared with a predetermined value in a comparison circuit.

9 Claims, 3 Drawing Figures

PROCESS FOR COATING GRANULAR MATERIALS

BACKGROUND OF THE INVENTION

This application is a continuation-in-part of our co-pending application Ser. No. 419,964, filed on Nov. 29, 1973, now abandoned, which is in turn a continuation-in-part of our abandoned application Ser. No. 213,608 filed on Dec. 29, 1971.

The present invention relates to a process for surface treatment of granular materials such as tablets, pills, china or porcelain, candies or other like articles which have an average particle size of from 100 to 1,000 microns and, more particularly, to a process for automatically coating such granular materials by the intermittent application of binding solution and by the continuous application of coating powder and drying air thereby to make coated products out of these granular materials.

So far as production of medicinal products in the pharmaceutical industry is concerned, one conventional coating process comprises applying an aqueous solution of sugar on the surface of tablets or pills fluidized within a rotating coating pan or column and subsequently or simultaneously drying the tablets or pills, already coated or being coated, with hot air to form a coating on each of the tablets or pills while they are still fluidized within the coating pan or column. Another conventional coating process comprises sequential repetition of a cycle of spraying binding liquid, distributing coating powder and applying hot air to form a coating on each of the tablets or pills while they are fluidized within a coating pan or column.

However, these conventional processes mentioned above have a number of disadvantages as follows:

1. A coating apparatus used in the practice of any of the conventional coating processes does not sufficiently and satisfactorily stir granular materials and this is true of the granular materials each having a particle size of less than 1,000 microns. Therefore, growth of uneven granules, formation of lumps of granules, prolonged coating time and/or other troubles are likely to occur. The worst of all is that resultant coated granules of the same quality cannot be obtained with respect to individual batch operations even if the identical operation has been effected to the granules of the individual batches.

2. No means are provided, particularly in case of the powder coating, for maintaining the optimum coating condition, the tolerance of which is narrowly limited and which is required to manufacture coated granules of uniform quality. Therefore, the quality of the coated products is considerably influenced by the skill of an attendant worker.

3. Wet granules have tend to adhere to the wall of the coating apparatus and also to stick together as a result of uneven supply of the coating liquid and/or rough stirring of the granules. This is particularly true when the optimum coating condition diverges from the tolerance.

4. Once one or some of the abovementioned troubles have occurred, removal of such troubles are manually performed by a skilled worker. This means that, according to the present-day engineering technique, automation of the conventional coating system is considered very difficult.

5. The globosity of each of the finished, coated products, that is, the ratio of the minor axis to the major axis of each coated granule, has been poor because of improper and insufficient shear force given to the granules being coated while being stirred in the coating apparatus.

6. One bath operation requires a coating time of about 5 to 10 hours, though the coating time varies depending on the size, quantity and other factors of materials to be coated.

In summary, the disadvantages inherent in the conventional processes are that the drying efficiency is poor, the stirring ability of the coating apparatus is so poor that lumps of the granules being coated are likely to result, and automation of the coating system is hard to achieve. In addition thereto, application of any of these conventional processes to fluidized bed coating tends to result in a substantial loss of a solution employed as a coating liquid, difficulty in maintenance of the optimum coating condition within its limited range of tolerance and difficulty in the application of coating powder.

SUMMARY OF THE INVENTION

Accordingly, an essential object of the present invention is to provide a novel process for coating granular materials, which substantially eliminates the disadvantages inherent in the conventional coating processes of a similar kind.

Another object of the present invention is to provide a process for coating granular materials, wherein supply of coating liquid or binding liquid is automatically controlled to attain the optimum coating condition while supply of coating powder is continuously effected in a varying amount.

A further object of the present invention is to provide a process for coating granular materials, wherein the proper amount of coating liquid or binding liquid is automatically supplied at the appropriate time while the granular materials to be coated are uniformly stirred with a proper and sufficient shear force developed among the granular materials, in order that the finished products are uniform with regards to the quality and granular size, have a good globosity and are free from formation of lumps of the granular material.

A still further object of the present invention is to provide a process for coating granular materials, wherein supply of the coating liquid or binding liquid is automatically controlled by detecting the wettability of the granular materials being coated, thereby to attain the optimum coating condition throughout the coating process.

A still further object of the present invention is to provide a process for coating granular materials, wherein, in order to attain the optimum coating condition, the wettability of the granular materials being coated is detected in terms of electrical resistance across each granular material and wherein the supply of the coating liquid or binding liquid is effected in response to the detected electro-resistance in such a way that, when said electro-resistance exceeds a predetermined value, said supply thereof is effected and, when said electro-resistance is lower than the predetermined value, said supply thereof is interrupted.

A still further object of the present invention is to provide a process for coating granular materials, which can be efficiently performed with relatively high reproducibility and which substantially reduces the coating time as compared with that required in the practice of any of the conventional coating processes.

To achieve the above mentioned objects of the present invention, it is an indispensable requirement that the granular materials to be coated are properly stirred and the supply of the coating liquid or binding liquid is properly controlled. As regards the stirring of the granular materials, it is necessary to perform this at a relatively high rate of stirring thereby to render the granular materials uniformly stirred with a proper shear force being distributed among the granular materials so that they are likely to separate and not to adhere to each other. This can be readily achieved by controlling the speed of rotation of the stirrer employed in the coating apparatus. In other words, stirring of the granular materials being coated must be performed in such a manner that all the granular materials are subjected to a relatively high shear force through the fluidization of the granular materials as well as the rotation of the individual granular materials while the relative speed of movement of these granular materials being fluidized in the coating apparatus is maintained in excess of a predetermined value.

In addition, the requirements for the stirring of the granular materials to be coated, supply of the coating liquid or binding liquid should be adequately controlled. In order to achieve this, a particular parameter should be chosen to effect automatic supply of the liquid in response to the wettability of the granular materials being coated.

For the particular parameter, according to the present invention, the specific electrical resistance of a mass of the granular materials being coated is employed. It is well known that the lower the electro-conductivity of a certain material, the higher the electro-resistance thereof, and this is true of the specific electro-resistance so far as a mass of such material is concerned. Hence, when the wettability of the granular materials being coated is low or high, the specific electro-resistance of the mass of the granular materials being coated is correspondingly high or low.

For detecting the wettability, that is, the specific electro-resistance, of a mass of the granular materials being coated, at least one electrode may be used as a positive electrode while an electro-conductive element forming a part of the coating apparatus and being in contact with the granular materials serves as a negative electrode. Alternatively, a pair of electrodes may be used if they are insulated from the electro-conductive element of the coating apparatus.

During practising of the coating process of the present invention in association with given granular materials to be coated, while a coating powder is continuously supplied into the coating apparatus throughout the whole period of time empirically required to complete the process for the given granular materials, supply of the coating liquid or binding liquid is intermittently performed in such a manner that, when the detected specific electro-resistance is higher than a predetermined value, such supply of the liquid is interrupted and, when the same is lower than the predetermined value, such supply of the liquid is initiated. For a given type of granular materials to be coated, this predetermined value for the specific electro-resistance fluctuates as the coating time passes due to the fact that the size of each grain of the granular material increases with a plurality of coated layers formed thereon.

An electro-magnetic value, for example, can be used to control the supply of the coating liquid or binding liquid to the coating apparatus in response to the wettability of the mass of granular materials measured in terms of the specific electro-resistance.

The wall adhesion of the granular materials used to occur as a result of direct contact of wet granular materials with the wall and the formation of lumps as a result of direct contact of the wet materials with each other, both due to the fact that the wettability of the granular materials being coated is relatively high which is observable immediately after supply of the liquid onto the granular materials being coated.

By controlling the supply of the coating liquid or binding liquid in the manner as hereinbefore described, adhesion of the granular materials which often occur on the wall of the coating apparatus during the coating operation and formation of lumps during the same time are first substantially eliminated.

Though, it is difficult that partial direct contact of wet granular materials with the wall or with each other granular materials is never eliminated perfectly by the conventional coating method or means.

Therefore, even if it is controlled the supply of the coating liquid or binding liquid, micro wet condition is never able to be controlled.

In principle, such wall adhesion and lump formation or caking both of any kind can be eliminated by continuous applying of dry powder onto the mass of the granular materials being coated.

It is the reason that the dry powder consists between bead and bead, bead and wall with the constant concentration protects from forming the liquid bridge by the wet bead or coating liquid.

However, adjustment of the amount of the dry powder required to eliminate the wall adhesion and/or caking is very difficult and, application of the dry powder in an amount greater or smaller than the required amount ultimately causes the finished products liable to some or all of the above mentioned disadvantages.

Furthermore, the rate of supply of the coating powder which is effected continuously during the coating time is made to increase in response to the increase of the particle size of each grain of the granular materials being coated. To this end, a programmer may be used to control the powder supply rate in accordance with a given program set in such programmer. Like the predetermined specific electro-resistance, the program for the control of the powder supply rate required for the given granular materials to be coated in relation to a given type of coating or binding liquid to be employed can empirically be determined.

Thus, by adequately controlling the timing of the supply of a constant amount of the coating or binding liquid and the rate of supply of the coating powder during the coating process, the optimum coating condition which is required to provide the coated granular materials of uniform quality with no lumps formed therein, can be advantageously attained.

The coating apparatus which can be employed in the practice of the process of the present invention may be of any known type so far as the above mentioned requirements to be achieved during stirring are satisfied. However, the employment of the coating apparatus disclosed in the U.S. Pat. No. 3,671,296, patented on June 20, 1972, is found to be the best at present, and therefore the coating apparatus of the above numbered U.S. patent is, in the description of the present invention, used as an example of a coating apparatus which satisfies the above requirements.

The employment of the coating apparatus of the above numbered U.S. patent in association with the process of the present invention has resulted in finished products of uniform quality and globosity, with substantial elimination of wall adhesion and lump formation, and also in reduction of the coating time to a time which is substantially 1/5 to 1/10 of that required by the conventional coating system.

It should be noted that the term, "wettability", hereinabove and hereinafter employed should be construed as meaning the moisture content present in the surface area of the outermost one of the layers coated on each grain of the granular materials.

BRIEF DESCRIPTION OF THE DRAWINGS

These and other objects and features of the present invention will become apparent from the following description taken in conjunction with a preferred embodiment thereof with reference to the accompanying drawings, in which.

DETAILED DESCRIPTION OF THE INVENTION

Figure 1:
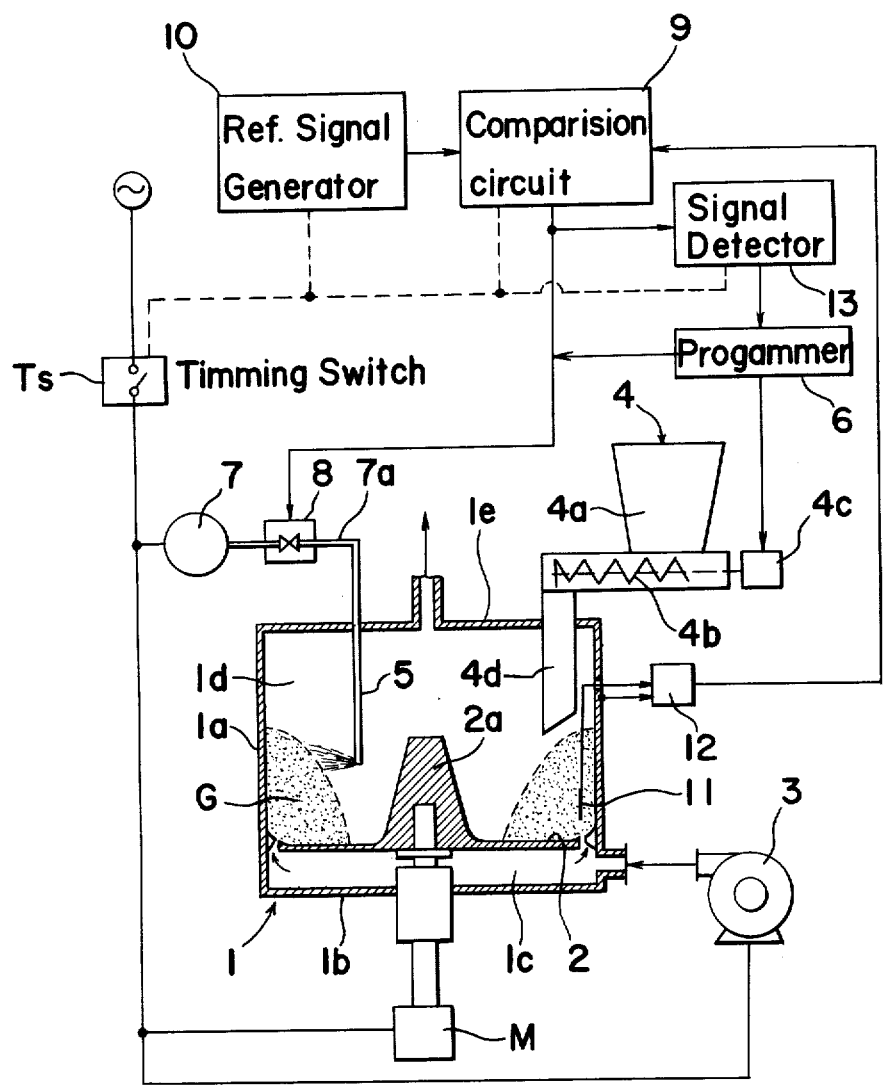
FIG. 1 is a block diagram showing a coating system by which the process of the present invention is practiced.

Referring first to FIG. 1, a coating apparatus which can be effectively used in the practice of the process of the present invention comprises a stationary vessel 1a having a lower open end closed by a bottom plate 1b which may be in contact with and rigidly mounted on a fixed framework (not shown) for support of the coating apparatus 1 in position. A rotatable dish 2 having an upwardly tapered projection 2a protruding therefrom at the center thereof is mounted within the vessel 1a in spaced relation to the bottom plate 1b and connected to a motor M through a drive shaft thereof which extends through the bottom plate 1b and is rigidly tapped into the rotatable dish 2 in alignment with the projection 2a. The stationary vessel 1a has a rising inner surface contiguous to the periphery of the rotatable dish 2 and curved upwardly therefrom to define a steadily rising surface from said dish 2.

The space defined at 1c between the bottom plate 1b and the rotatable dish 2 within the vessel 1a is communicated to an air blower 3 from which drying air can be supplied to the interior of the vessel 1a via an annular gap between the rising inner surface of said vessel 1a and the periphery of the rotatable dish 2, said interior of the vessel 1a being designated by 1d.

The coating apparatus 1 is designed such that, during operation thereof with a mass of granular materials G to be coated therein, rotation of the rotatable dish 2 moves the granular materials up the continugous and rising inner surface of the vessel 1a whereby said granular materials are circulated from said dish 2, up said inner surface and back to said dish 2.

The details of arrangement and operation of the coating apparatus 1 are fully disclosed in the previously mentioned U.S. patent and, therefore, are herein omitted for the sake of brevity.

Referring still to FIG. 1, in accordance with the teachings of the present invention, the coating apparatus 1 of the above construction is provided with a powder supply unit 4 which includes a hopper 4a, a screw conveyor 4b driven by a motor 4c and a powder duct 4d and which operates in such a manner as to feed coating powder onto a fluidized mass of granular materials G within the interior 1d of the vessel 1a from the hopper 4 through the powder duct 4d via the screw conveyor 4b. The motor 4c for driving the screw conveyor 4b is continuously operated during the whole coating time, the speed of rotation of the motor 4c being controlled by a programmer 6 to cause the rate of supply of coating powder to follow a predetermined program shown in FIG. 2, i.e., to increase in proportion to an increase of the size of each grain of the granular materials G being coated.

More specifically, the motor 4c for the screw conveyor 4b commences to operate in response to an input signal fed from the programmer 6 and ceases to operate in response to discontinuance of said input signal from said programmer 6, the level of said input signal varying in accordance with a predetermined program set in said programmer 6, i.e., to increase the rate of supply of the coating powder as the coating time passes.

The motor M for driving the rotatable dish 2 and the air blower 3 for feeding drying air to the space 1c in the vessel 1a, which are respectively operated at a predetermined speed, are both connected to a power source through a timing switch TS, the operation thereof being determined by the setting of said timing switch TS which may be equal to or longer than the required coating time.

A spray nozzle 5 for spraying a solution of coating or binding liquid onto the mass of the granular materials being coated within the vessel 1a is communicated to a source 7 of the solution through a pipe line 7a. The solution source 7 may be composed of an electrically operated hydraulic pump and a reservoir for the solution and is also connected to the power source through the timing switch TS and is, therefore, operated in synchronism with either of the motor M and blower 3. The pipe line 7a includes an electromagnetic valve 8 disposed therein between the source 7 and the nozzle 5 for selectively opening and closing said pipe line 7a in a manner as will be described later for controlling supply of the coating or binding solution to be fed under pressure onto the fluidized mass of the granular materials G within the interior 1d of the vessel 1a in response to a control pulse from a comparison circuit 9, the function of which will be described later.

In the embodiment illustrated, a single positive electrode 11 is employed for detecting the specific electro-resistance of the fluidized mass of the granular materials G being coated. This electrode 11 is held within the interior 1d of the vessel 1a and in the path of travel of the mass of the granular materials G moving within said vessel 1a during rotation of the rotatable dish 2, and spaced from the inner surface of said vessel 1a a predetermined distance preferably corresponding to more than the size of each of the finished coated granular materials, said inner surface serving as a ground or negative electrode.

The positive electrode 11 and a portion of the inner surface of the vessel 1a which serves as the ground or negative electrode are electically connected to a detector 12 which measures the specific electro-resistance of the fluidized mass of the granular materials being coated and generates a signal indicative of the measured specific electro-resistance. The signal from the detector 12 is subsequently supplied to the comparison circuit 9. The comparision circuit 9 acts to compare the actually measured specific electro-resistance with a reference or predetermined value fed from a reference signal generator 10 and then to generate a control pulse of a duration corresponding to the period during which the measured specific electro-resistance is in excess of the reference value. The electromagnetic valve 8, upon receipt of the control pulse from the comparison circuit 9, operates to open the pipe line 7a thereby to permit the spray nozzle 5 to spray the coating or binding solution, fed under pressure from the source 7 to said spray nozzle 5, onto the fluidized mass of the granular materials. The spraying of the coating or binding solution continues during the duration of the control pulse fed from the comparison circuit 9 to said electromagnetic valve 8. In other words, generation of the control pulse from the comparison circuit 9 takes place each time the highest possible specific electro-resistance detected by the detector 12 during each interval in which no supply of the coating or binding solution is effected commences to exceed the predetermined value and ceases at the time the detected specific electro-resistance after having attained its peak value upon completion of wetting of the granular materials being coated substantially falls below the predetermined value.

More specifically, during each interval in which no supply of the coating or binding solution is effected through the nozzle 5 onto the fluidized mass of the granular materials G, the detected specific electro-resistance increases as each of the granular materials being coated is dried. The lower the wettability, the higher the detected specific electro-resistance. However, in practice, the increase of the detected specific electro-resistance continues for a certain period of time immediately after supply of the coating or binding solution is effected, because it requires such period of time for each grain of the granular materials G to become wetted by the applied coating or binding solution while they are subjected to the drying air fed from the blower 3 through the space 1c below the rotatable dish 2. As the wettability increases, the detected specific electro-resistance begins to decrease and then to drop below the predetermined value at which time the supply of the coating or binding solution is stopped, i.e., at which time the duration of the control pulse from the comparison circuit 9 to the electromagnetic valve 8 expires.

Therefore, the reference value, the signal indicative of which reference value is fed to the comparison circuit 9 from the reference signal generator 10, is selected such that the moisture content in the outermost coated layer on each grain of the granular materials represents a predetermined value within the range of 10 to 50% by weight relative to the total weight of the powder that has been used to form such outermost coated layer.

Figure 2:
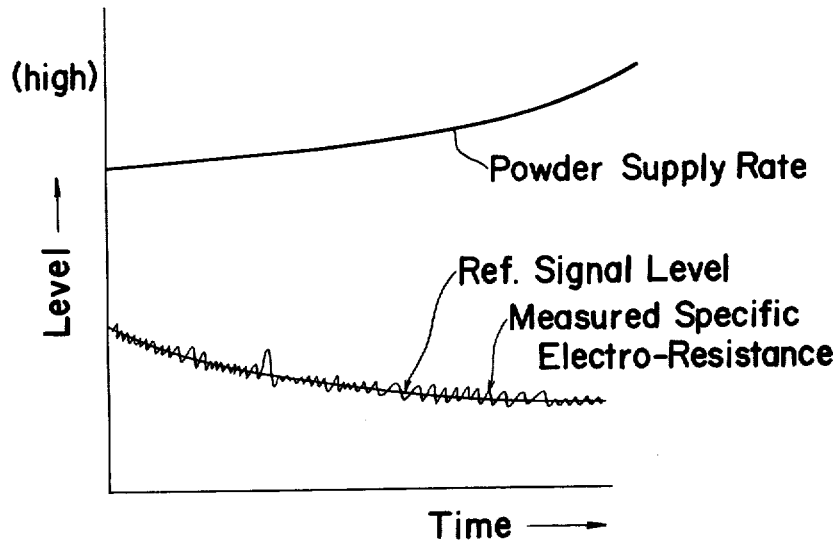
FIG. 2 is a schematic program chart showing the interrelation between the rate of supply of coating powder and the level of a reference signal with which a measured specific electro-resistance is compared.

Furthermore, irrespective of the wettability of the granular materials, increase of the size of each of the granular materials being coated which is observable during the coating process results in fluctuation of the mean value of the detected specific electro-resistance as the coating time passes. Therefore, the reference value set in the reference value signal generator 10 is made to correspondingly vary, as shown in the chart of FIG. 2, in order to maintain the moisture content within the range of 10 to 50 wt.% relative to the total weight of the powder throughout the coating operation. In other words, even though the level of the reference value with which the detected specific electro-resistance is compared in the comparison circuit 9 varies as the coating time passes, the moisture content can be maintained at the predetermined value within the range of 10 to 50 wt.% relative to the total weight of the powder used to form each coated layer on the granular materials being coated.

In practice, for a given granular material, coating powder and concentration of the coating or binding solution, the rate of supply of the coating powder and the amount of the coating or binding solution supplied each time the measured specific electro-resistance exceeds the reference value are interrelated with each other. Therefore, it is highly desirable to determine the program to be set in the programmer 6 for the powder supply rate and the reference value to be set in the reference signal generator 10 for the amount of the coating or binding solution, in consideration of the above mentioned interrelation and in such a way that the optimum coating condition can be achieved in the coating apparatus during the coating operation with no substantial wall adhesion and formation of lumps. Usually, once the powder supply rate has been determined on the basis of data available during the course of experiments, the reference value can easily be determined.

It should be noted that, in the chart of FIG. 2, the wavy line overlapping the curve indicative of fluctuation of the reference value set in the reference signal generator 10 in association with the specific electro-resistance indicates variation of specific electro-resistance detected during the coating operaton of the fluidized mass of the granular materials G being coated.

The programmer 6 for controlling the powder supply rate ceases to generate the signal required to drive the motor 4c for the screw conveyor 4b at the end of the program, i.e., upon expiration of the preset coating time. This programmer 6, however, begins to operate upon receipt of an output signal from a signal detector 13 that detects the first generation of the control pulse from the comparision circuit 9 which takes place substantially after the first application of the coating or binding solution through the nozzle 5 onto the mass of the granular materials G. This signal generator 13 may be composed of a self-energizable electromagnetic switch and continues to generate the output signal to the programmer 6 so long as it is energized.

From the foregoing description, it is clear that the coating system according to the present invention operates in the following manner.

Assuming that the timing switch TS is set to operate for the required coating time with the source 7, the motor M and the blower 3 connected to the power source, and that the various electrical circuits except for the programmer 6 are operated, the system is ready to perform a coating operation while the rotatable dish 2 within the vessel 1a is rotated about the motor shaft. Immediately after a predetermined amount of granular materials to be coated has been charged into the interior 1d of the vessel 1a with a covering 1e closing the upper opening of said vessel 1a, a signal indicative of a specific electro-resistance of the fluidized mass of the granular materials G flows from the electrode 11 to the detector 12 from time to time, which is in turn fed to the comparison circuit 9. The granular materials G charged into the interior 1d of the vessel 1a are gradually dried by the application of drying air fed from the blower 3 and, therefore, the specific electro-resistance detected by the electrode 11 gradually increases.

At the time the level of the signal indicative of the detected specific electro-resistance exceeds the level of a reference signal fed from the reference signal generator 10, the comparision circuit 9 generates a control pulse. This control pulse from the comparision circuit 9 is fed to the electromagnetic valve 8 thereby permitting the latter to open the pipe line 7a to spray coating or binding solution at a constant rate through the nozzle 5 onto the fluidized mass of the granular materials G. The generation of the control pulse continues until the detected specific electro-resistance that has exceeded the predetermined value falls below said predetermined value.

Simultaneously with the first generation of the control pulse from the comparision circuit 9, the signal detector 13 is triggered onto generate an output signal and feeds it to the programmer 6. The programmer 6, upon receipt of the output signal from the signal detector 13, generates a signal therefrom to the motor 4c for the screw conveyor 4b whereby the latter is operated at a predetermined variable speed to supply coating powder from the hopper 4a onto the fluidized mass of the granular materials G in accordance with a program set in the programmer 6. Once the programmer 6 is operated in response to the signal from the signal detector 13, the programmer 6 continues to drive the motor 4c until the termination of the program set in the programmer 6 so that the coating powder is continuously supplied at the predetermined powder supply rate shown in FIG. 2.

Thereafter, each time the detected specific electro-resistance exceeds the predetermined value, spraying of the coating or binding solution takes place while the coating powder is continuously supplied. Upon termination of the generation of the signal from the programmer 6, not only does the motor 4c ceases to operate, but also the programmer 6 generates a signal which is fed to the electromagnetic valve 8 to operate the latter to close the pipe line 7a. Simultaneously therewith or subsequently, the preset coating time set in the timing switch TS expires and, therefore, no supply of power to the source, the motor M and the blower 3 takes place.

As hereinbefore described, although the process of the present invention is applicable satisfactorily and effectively to coating of the granular materials having a particle size of from 100 to 1,000 microns, the granular materials to be coated by the process of the present invention are preferred to have a particle size within the range of from 300 to 1,000 microns.

The present invention will now be described by way of examples which are not intended to limit the scope of the present invention.

EXAMPLE I

Seed beads, one unit of granulated saccharose coated with one unit of corn-starch, were charged in an amount of 2 kg. into a coating apparatus of the construction shown in FIG. 1 having a rotatable dish of 360 mm. in diameter and capable of rotating at 180 rpm. Each seed bead was 580 microns in initial mean diameter and had a globosity of 0.7. Ascorbic acid was continuously supplied at the minimum powder supply rate of 40 g/min. and the maximum powder supply rate of 100 g/min. by the programmer in accordance with a predetermined program. The total amount of ascorbic acid used as the coating powder was 3.7 kg. A syrup containing 66.6% saccharose and 33.4% water was used as the binding liquid and was supplied at a mean rate of 22 ml/min. and each time the detected specific electro-resistance exceeded the predetermined value represented by a curve shown in FIG. 3. The total amount of the binding liquid used was 1.14 liters. The period required for stirring the granular materials in the coating apparatus was 50 minutes.

The uniformly finished products were obtained with the globosity thereof being 0.97. The yield factor of the coating powder was 98%. The average size of the finished products was 980 microns in diameter. The air volume velocity required to spray the binding solution was 1.6 m³/hr. The blower was operated to feed drying air at 10 m³/hr. and the temperature of the drying air used was room temperature. 99.5% of the total amount of the finished products were found excellent.

EXAMPLE II

Seed beads, one unit of granulated saccharose coated with one unit of corn-starch, were charged in an amount of 2 kg. into the same coating apparatus as used in EXAMPLE I. Each seed bead was 665 microns in initial mean diameter and had a globosity of 0.7. Calcium-panthothenate was, as a coating powder, supplied at the minimum powder supply rate of 46 g/min. and the maximum powder supply rate of 120 g/min. by the programmer in accordance with a predetermined program. The total amount of the coating powder used was 5.7 kg. The same syrup used in EXAMPLE I was supplied at a mean rate of 11.5 ml/min. and each time the detected specific electro-resistance exceeded the predetermined value represented by a curve shown in FIG. 3. The total amount of the binding liquid used was 2.3 liters. The period required for stirring the granular materials in the coating apparatus was 20 minutes. The air volume velocity required to spray the binding solution was 1.5 m³/hr. and the blower was operated to feed drying air of room temperature at 10 m³/hr.

The uniformly finished products were obtained with the globosity thereof being 0.9. The average size of the finished products was 950 microns in diameter. The yield factor of the coating powder was 96% and 99.7% of the total amount of the finished products were found excellent.

EXAMPLE III

Seed beads, one unit of granulated saccharose coated with one unit of corn-starch, were charged in an amount of 20 kg. into a coating apparatus of the construction shown in FIG. 1 having a rotatable dish of 1,000 mm. in diameter and capable of rotating at 60 rpm. Each seed bead was 580 microns in initial mean diameter and had a globosity of 0.72. As a coating powder, Thiamine-tetrahydro-furyl disulfide (TTFD) was continuously supplied at the minimum powder supply rate of 400 g/min. and the maximum powder supply rate of 800 g/min. by the programmer in accordance with a predetermined program. The total amount of the coating powder used was 28 kg. The same syrup as employed in the foregoing examples was supplied as a binding solution at a mean rate of 241 ml/min. and each time the detected specific electro-resistance exceeded the predetermined value represented by a curve shown in FIG. 3. The total amount of the binding solution used was 10.85 liters. The period required for stirring the granular materials in the coating apparatus was 45 minutes. The air volume velocity required to spray the binding solution was 15 m³/hr. and the blower was operated to feed drying air of room temperature at 10 m³/hr.

The uniformly finished products were obtained with the globosity thereof being 0.97. The average size of the finished products was 920 microns in diameter. The yield factor of the coating powder was 98% and 99.9% of the total amount of the finished products were found excellent.

EXAMPLE IV

Seed beads, saccharose crystal, were charged in an amount of 2 kg. into a coating apparatus of the construction shown in FIG. 1 having a rotatable dish of 360 mm. in diameter and capable of rotating at 240 rpm. Each seed bead was 200 micron in initial mean diameter and had a globosity of 0.6. Corn-starch was continuously supplied at the minimum powder supply rate of 10 g/min. and the maximum powder supply rate of 60 g/min. by the programmer in accordance with a predetermined program. The total amount of corn-starch used as the coating powder was 2.2 kg.

Figure 3:
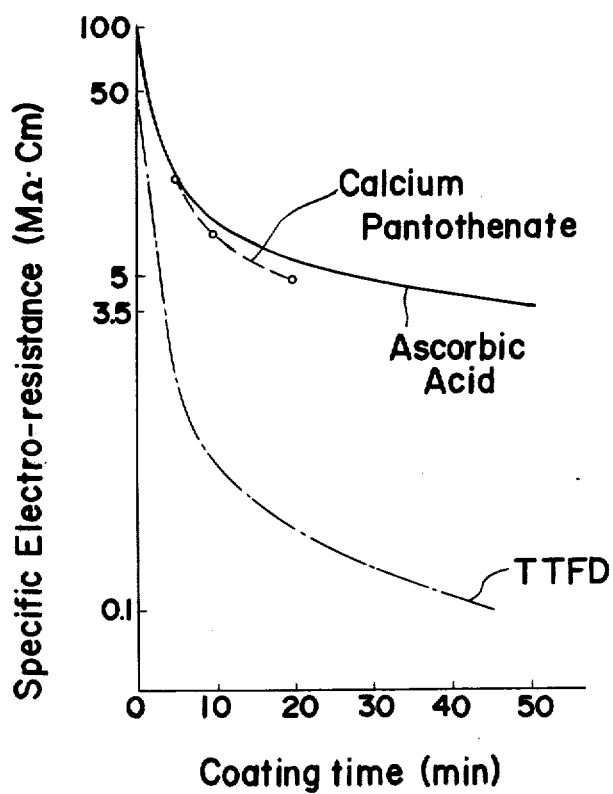
FIG. 3 is a program chart showing the levels of reference signals associated with the use of ascorbic acid, calcium panthothenate and TTFD for coating powder, respectively.

A syrup containing 45% saccharose and 55% water was used as the binding liquid and was intermittently supplied at a mean rate of 10 ml/min. and each time the detected specific electro-resistance exceeded the predetermined value represented by a curve shown in FIG. 3. The total amount of the binding liquid used was 0.96 liters. The period required for stirring the granular materials in the coating apparatus was 62 minutes.

The uniformly finished products were obtained with the globosity thereof being 0.83. The yield factor of the coating powder was 98.7%. The average size of the finished products was 620 microns in diameter. The air volume velocity required to spray the binding solution was 1.6 m³/min. The blower was operated to feed drying air of room temperature at 10 m³/min. 97.5% of the total amount of the finished products was found excellent.

The following comparisons are based on the conventional processes and are intended to demonstrate the efficiency and effectiveness of the present invention by comparision.

Comparison I

Seed beads, one unit of granulated saccharose coated with one unit of corn-starch, were charged in an amount of 2 kg. into a coating apparatus of a construction shown in FIG. 1 having a rotatable dish of 360 mm. in diameter and capable of rotating at 180 rpm. Each seed bead was 580 microns in initial mean diameter and had a globosity of 0.7. These granular materials were coated by the known automatic process wherein solution spraying, powder supplying and air supplying are automatically sequentially repeated. In the employed method for this comparision, each cycle comprises solution spraying for 3 minutes, powder supplying for 5 minutes and drying for 5 minutes and this cycle was repeated 74 cycles requiring a total period of approximately 16 hours. During the coating operation in accordance with this known process, ascorbic acid was, as a coating powder, supplied at the rate of 10 g/min. and the total amount of the coating powder used was 3.7 kg. As a binding solution, the same syrup as employed in the foregoing examples was supplied at the rate of 10 ml/min. and the total amount of the binding solution used was 2.22 liters. The drying air of approximately 60° C. was supplied at 40 m³/hr. each 5 minutes.

It was found that most of the finished products were scratched and the globosity thereof was 0.80. The average size of the finished products were 930 microns in diameter and 25% of the total amount of the finished products were found unacceptable while the yield factor of the coating powder was 78%.

Comparision II

Seed beads of the same size as in the foregoing comparision were charged in the same amount as in the foregoing comparision into a conventional coating pan, 10 inches in diameter and capable of rotating at 42 rpm. The process employed was similar to that of the foregoing comparision. The coating operation was unable to operate over 5 cycles because of considerable formation of lumps in the coating pan.

Comparision III

Seed beads of the same size as in the Example I were charged in the same amount as in the Example I into a conventional coating pan, 10 inches in diameter and capable of rotating at 42 rpm. Except for the use of the conventional coating pan, a process identical with that employed in the Example I was employed. The coating operation had failed by the time five minutes elapsed, because of formation of lumps within the conventional coating pan.

Comparision IV

Seed beads, one unit of granulated saccharose coated with one unit of corn-starch, were charged in an amount of 2 kg. into a coating apparatus of the construction shown in FIG. 1 having a rotatable dish of 360 mm. in diameter and capable of rotating at 180 rpm. Each seed bead was 580 microns in initial mean diameter and had a globosity of 0.7. Ascorbic acid was continuously supplied at the rate of 70 g/min. A syrup of the same composition as in the Example I was used as the binding solution and was supplied each time the detected specific electro-resistance exceeded a fixed predetermined value of 30 Mega-ohm.cm.

As a result, the yield factor of the coating powder was 88% and each of the finished products had a globosity of 0.90 and a final diameter of 960 microns on average. 5% of the total amount of the coating powder used was caked to the wall surface of the coating apparatus.

Comparision V

Seed beads, one unit of granulated saccharose coated with one unit of corn-starch, were charged in an amount of 2 kg. into a coating apparatus of the construction shown in FIG. 1 having a rotatable dish of 360 mm. in diameter and capable of rotating at 180 rpm. Each seed bead was 580 microns in initial mean diameter and had a globosity of 0.7. Ascorbic acid was intermittently supplied at a variable rate within the range of 40 g/min. at minimum to 100 g/min. at maximum together with the binding liquid by the programmer in accordance with a predetermined program. The total amount of the ascorbic acid used as the coating powder, was 3.7 kg. The binding liquid contained 66.6% saccharose and 33.4% water and the rate of supply thereof was within the range of 13 ml/min. at minimum to 31.5 ml/min. at maximum. The supply of the binding liquid was controlled by the programmer in accordance with a predetermined program. The ratio of the binding liquid relative to the powder was accordingly 0.315 (ml/g).

The air volume velocity required to spray the binding solution was 1.6 m³/hr. The blower was operated to feed drying air of 60° C. at the rate of 20 m³/hr.

The operated cycle and the result are shown in Table 1.

The powder and syrup feed rate of Lot. No. 6 was within the range of 200 g/min. at minimum to 624 g/min. at maximum and of 62.8 ml/min. at minimum to 197 ml/min., respectively.

As can readily be seen from Table 1, in spite of long time operation of gradual feeding for the purpose of lessening lump formation and sticking, it was found that the Lots. Nos. 1 to 3 gave unsatisfactory and scratched products. The finished products identified by Lots. Nos. 4 to 6 were unacceptable for the practical use.

specific electro-resistance is in excess of said reference value, said binding solution spraying being effected under a predetermined pressure onto the fluidized mass of said granular material by means of an electromagnetic valve opened by said control pulse during the duration of said control pulse, the electromagnetic valve being closed to discontinue spraying when the detected specific electro-resistance is less than the reference value and no control pulse is generated from said comparision circuit, and feeding coating powder continuously throughout the coating operation onto the fluidized mass of said granular material within said vessel.

2. A process as claimed in claim 1, wherein the rate of continuous supply of the coating powder increases as the coating time passes in accordance with a predetermined program.

3. A process as claimed in claim 1, wherein said reference value is selected, in consideration of the rate of supply of the coating powder, such that the moisture

TABLE 1

| Lot No. | Simulteneous Feed of Powder & Liquid | Interval Between Power-Liquid Feed & Drying | Drying Time | Total Coating Time | Sticking & Lump Formation | Final Globosity | Final Particle Size |
|---|---|---|---|---|---|---|---|
| 1 | 30 sec. | 30 sec. | 2 min. | 420 min. | 25% | 0.70 | 950 μ |
| 2 | " | " | 5 min. | 634 min. | 23% | 0.72 | |
| 3 | 20 sec. | 20 sec. | 2 min. | 434 min. | 18% | 0.69 | |
| 4 | Continuously | 0 | 0 | 53 min. | 60% | 0.80 | |
| 5 | " | 0 | Continuously | " | 69% | 0.78 | |
| 6 | 30 sec. | 30 sec. | 2 min. | 54 min. | 80% | 0.75 | |
| Ex* | — | — | — | 53 min. | 0.1% | 0.98 | |

Ex* Reference data obtained by the process of the present invention.

Although the present invention has been fully described by way of example, it should be noted that various changes and modifications are apparent to those skilled in the art. For example, it is obvious to those skilled in the art that a pair of electrodes may be used to detect the specific electro-resistance of the mass of the granular materials being coated. Therefore, such changes and modifications should be construed as included within the true scope of the present invention unless they depart therefrom.

What is claimed is:

1. A process for coating granular material having granules with a particle size within the range of 100 to 1,000 microns in a coating apparatus of the type having a rotatable dish, which dish is mounted in a stationary vessel, said stationary vessel having a rising inner surface contiguous to the periphery of said dish and curved upwardly therefrom to define a steadily rising surface from said dish, which comprises charging said granular material into said vessel and onto said rotatable dish while said rotatable dish is rotated at a predetermined speed, intermittently supplying a binding solution to said vessel by measuring the specific electro-resistance of a mass of said granular material by means of a detector including at least one electrode which is spaced from a portion of the rising inner surface of the vessel, feeding a signal indicative of the detected specific electro-resistance to a comparision circuit, comparing said signal from said detector with a reference value fed from a reference signal generator, said comparision circuit generating a control pulse only when said detected specific electro-resistance exceeds the reference value and continuing the generation of such control pulse during a period in which said detected content of said granular material being coated is a predetermined value within the range of 10 to 50% by weight relative to the total amount of the coating powder used to form each outermost layer on said granular material.

4. A process as claimed in claim 2, wherein said reference value is selected, in consideration of the rate of supply of the coating powder, such that the moisture content of said granular material being coated is a predetermined value within the range of 10 to 50% by weight relative to the total amount of the coating powder used to form each outermost layer on said granular material.

5. A process as claimed in claim 1, wherein said supply of the coating powder is initiated in response to the first generation of said control pulse.

6. A process as claimed in claim 1, further comprising a step of applying drying air continuously throughout the coating operation onto the fluidized mass of the granular material within said vessel.

7. A process as claimed in claim 2, further comprising a step of applying drying air continuously throughout the coating operation onto the fluidized mass of the granular material within said vessel.

8. A process as claimed in claim 3, further comprising a step of applying drying air continuously throughout the coating operation onto the fluidized mass of the granular material within said vessel.

9. A process as claimed in claim 4, further comprising a step of applying drying air continuously throughout the coating operation onto the fluidized mass of the granular material within said vessel.

* * * * *